United States Patent [19]

Katz et al.

[11] Patent Number: 5,028,435
[45] Date of Patent: Jul. 2, 1991

[54] SYSTEM AND METHOD FOR TRANSDERMAL DRUG DELIVERY

[75] Inventors: Martin Katz, Menlo Park; Sergio Nacht, Los Altos; Jorge Heller, Woodside, all of Calif.

[73] Assignee: Advanced Polymer Systems, Inc., Redwood City, Calif.

[21] Appl. No.: 355,718

[22] Filed: May 22, 1989

[51] Int. Cl.⁵ .................. A61K 9/14; A61K 13/02
[52] U.S. Cl. ............................ 424/484; 424/447; 424/448; 424/449; 424/486
[58] Field of Search ............. 424/484, 448, 486, 447, 424/449

[56] References Cited

U.S. PATENT DOCUMENTS

| 3,797,494 | 3/1974 | Zaffaroni | 424/448 |
| 4,687,481 | 8/1987 | Nuwayser | 604/897 |
| 4,783,335 | 11/1988 | Lipshitz | 424/407 |

Primary Examiner—Thurman K. Page
Assistant Examiner—G. S. Kishore
Attorney, Agent, or Firm—Townsend and Townsend

[57] ABSTRACT

Transdermal drug delivery systems comprise a backing or enclosure having a matrix layer which incorporates a drug and a percutaneous enhancer for the drug. The percutaneous enhancer and/or drug will be contained within polymeric particles dispersed through the matrix layer, where the polymeric particles define pore networks which are sized to release the enhancer and/or drug into the matrix layer at rate(s) selected to provide for a desired rate of drug penetration. By isolating the enhancer within the polymeric particles, adverse interactions between the enhancer and the matrix layer and/or the drug can be minimized. Moreover, the release rate of the enhancer into the matrix layer can be carefully controlled, which in turn controls the penetration rate of the drug into the treated host.

36 Claims, 1 Drawing Sheet

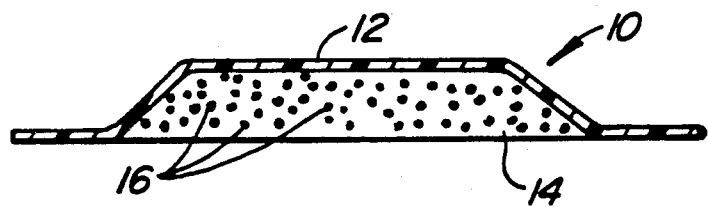
FIG._1.
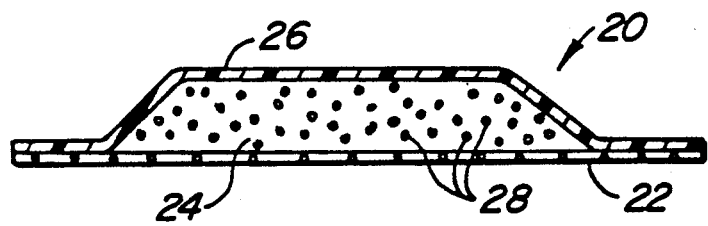
FIG._2.
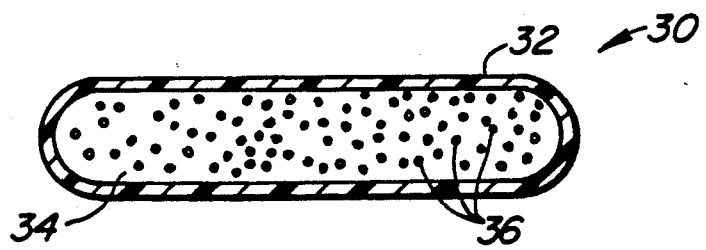
FIG._3.
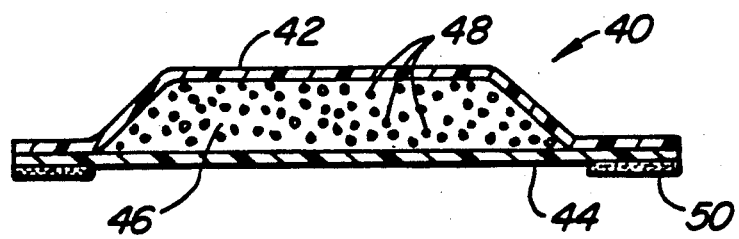
FIG._4.

SYSTEM AND METHOD FOR TRANSDERMAL DRUG DELIVERY

BACKGROUND OF THE INVENTION

1. Field of the Invention

The present invention relates generally to systems and methods for the transdermal administration of drugs and more particularly to the use of porous, non-collapsible polymeric particles for containing the drugs and/or percutaneous drug enhancers within a matrix layer of a transdermal drug delivery device.

Transdermal delivery is a preferred route of drug administration under a variety of circumstances. Transdermal delivery is accomplished by exposing a source of the drug to a patient's skin for an extended period of time. Typically, the drug is incorporated in a matrix or reservoir from which it is released onto the patient's skin. The rate of release can be controlled by a membrane placed between the reservoir and the skin, by diffusion from a monolithic device, or by the skin itself serving as a rate-controlling barrier in the delivery system. Transdermal delivery enjoys a number of advantages including optimization of systemic concentration, enhanced therapeutic efficacy, reduced frequency of dosage, reduced side effects, and hepatic bypass which can increase the effective activity of the drug.

Numerous factors must be considered when designing systems for transdermal drug delivery. Of particular interest to the present invention, the rate of drug delivery to the skin and rate of penetration of the drug through the skin must be carefully controlled in order to optimize a particular drug therapy. The rate at which the drug is delivered from the device to the skin is most advantageously controlled by the use of rate-limiting membranes which are placed between the drug reservoir and the skin. Assuming that the skin is sufficiently permeable to the drug (i.e., absorption through the skin is greater than the rate of passage through the membrane), the membrane will serve to control the dosage rate experienced by the patient. In the case of relatively non-permeable drugs, however, the situation is somewhat more complex. Where a desired drug cannot be transported across the skin at a sufficiently high rate to achieve a therapeutically useful blood concentration, various ionophoretic and chemical approaches have been proposed to enhance drug permeability. Of particular interest to the present invention, chemical permeability enhancers can be administered simultaneously with the drug in order to increase the transport of drug through the stratum corneum.

Most commonly, the chemical permeability enhancer will be combined with the drug in the reservoir or matrix layer of transdermal delivery device. The enhancer is then released under similar kinetics as the drug so that the concentrations of the drug and the enhancer at the skin interface cannot be independently controlled other than by varying their respective initial concentrations. The inability to separately control the release rates of drug and enhancer renders the design of transdermal delivery systems much more difficult. For example, it may be necessary to provide excess drug and/or enhancer in order to achieve the concentration necessary to effect a desired release rate.

In order to improve control over the rate of drug delivery from a transdermal device and through a patient's skin, it would be desirable to provide devices which decouple the release rate of the drug from the release rate of the chemical permeability enhancer. In particular, it would be desirable to provide such transdermal delivery devices which allow both the amount and the release rate of both the drug and the chemical enhancer to be independently controlled within the device. In this way, the use of excess drug and/or enhancer will not be required and efficient drug utilization can be maximized.

2. Description of the Background Art

U.S. Pat. No. 4,687,481, describes a transdermal drug delivery system including a backing sheet and a macroporous face membrane having a reservoir therebetween. The reservoir contains an occlusive liquid base material having a plurality of drug-containing particles dispersed therein. The particles are in the form of drug-polymer solids or polymer-coated drug particles. U.S. Pat. No. 4,692,462, discloses the use of charged ion exchange resins for containing drugs within a transdermal delivery system. Salt concentration within a gel layer including the resin is varied to control the drug release rate. U.S. Pat. Nos. 3,797,494 and 3,731,683, disclose transdermal patches where drugs are incorporated in microcapsules dispersed in an adhesive layer. The drug release rate is controlled by diffusion from the microcapsules. U.S. Pat. No. 3,854,480, discloses a drug delivery reservoir device where solid drug particles are dispersed in a solid reservoir layer within a rate controlling membrane. German patent application DE 3333444A1 describes a transdermal patch having a gelatin matrix layer where the active substance is applied to a particulate carrier. Japanese patent application 59-84812 discloses a controlled release device having a drug-containing powder dispersed in a resinous sheet. EPO 226 240 discloses a topically applied emulsion having a bioactive agent-containing particulates dispersed therein. EPO 241 178 discloses antibiotics in polymeric particulates dispersed in a wafer-soluble polymer for application to the gums. The following U.S. Pat. Nos. are also of interest: 4,764,382; 4,747,845; 3,993,073; 3,948,254; 3,948,262; and 3,598,122.

SUMMARY OF THE INVENTION

Systems and methods for the rate-controlled delivery of drugs to vertebrate hosts are provided. The systems comprise a matrix layer having a backing or disposed within an enclosure, where at least a portion of the enclosure is permeable to the drug(s) to be administered as well as to a chemical penetration enhancer which promotes transport of the drug across a skin or membrane area of the host. The drug and the enhancer are present in the matrix layer, and the system will usually further comprise means for securing the system to the skin, such as a tape or adhesive layer, but may also be in the form of an insert, lozenge, implant, or the like, requiring no specific means for attachment.

According to the present invention, at least a portion of either the drug or the chemical penetration enhancer (or both) will be contained within a plurality of polymeric particles dispersed within the matrix layer. The polymeric particles comprise non-collapsible, crosslinked structures defining a network of internal pores which entrap and release the drug and/or enhancer into the matrix at a preselected rate, whereby the relative release rate of enhancer to drug determines the rate at which the drug is transported across the skin or membrane.

In the preferred embodiment, the chemical penetration enhancer is present in the polymeric particles while the drug is present as a liquid or solid within the matrix layer. The drug is present in an amount and concentration which exceeds the absorptive capacity of the host skin or membrane, and the rate of systemic drug delivery is controlled by controlling the release rate of enhancer into the matrix. Release of the enhancer into the matrix layer can be controlled independently of the drug concentration by selecting the physical characteristics of the particles, which determine the enhancer release rate into the matrix. Alternatively, the drug may also be contained within polymeric particles. By properly selecting the release rates from each set of particles, release of both the enhancer and the drug into the matrix can be independently controlled, allowing optimization of the ratio of delivery rates.

A particular advantage of the present invention is found in the isolation of the enhancer from the matrix layer. Due to the solvating nature of the enhancer, there is frequently an adverse chemical interaction between the enhancer and the matrix layer. This is particularly true when the matrix layer is the adhesive layer which adheres to the skin in an adhesive patch structure. The isolation of the enhancer within the dry polymeric particles of the present invention minimizes any such interference. Moreover, the slow release rate over an extended period of time further minimizes any adverse impact that relatively high concentrations of the enhancer would otherwise have.

BRIEF DESCRIPTION OF THE DRAWINGS

FIG. 1 illustrates a transdermal adhesive device constructed in accordance with the principles of the present invention. The polymeric particles containing the percutaneous enhancer and/or drug are dispersed in an adhesive matrix which is secured directly to the skin or membrane of the host.

FIG. 2 illustrates a monolithic transdermal delivery system constructed in accordance with the principles of the present invention. The polymeric particles containing the percutaneous enhancer and/or drug are dispersed in a matrix layer which is separate from an adhesive layer.

FIG. 3 illustrates a reservoir transdermal delivery system constructed in accordance with the principles of the present invention. The polymeric particles containing the percutaneous enhancer and/or drug are dispersed in a reservoir matrix which is contained within a membrane which is permeable to the drug and the enhancer.

FIG. 4 is an alternate construction for a reservoir device, where a peripheral adhesive layer is provided on the membrane which encloses the reservoir matrix.

DESCRIPTION OF THE SPECIFIC EMBODIMENTS

The drug delivery systems of the present invention include a matrix layer and a backing or enclosure, where the matrix layer contains the drug and an enhancer selected to promote transport of the drug across a skin or membrane area of the treated host. At least one of the drug and the enhancer is contained within a plurality of polymeric particles dispersed throughout the matrix layer, where the particles release the drug and/or enhancer at rates selected to provide the desired rate of transdermal transport of the drug. Preferably, only the enhancer will be present in the polymeric particles and the drug will be present directly in the matrix as a solid or liquid. The release rate of the enhancer from the polymeric particles will be the rate limiting factor in determining the rate of drug delivery.

The backing or enclosure of the drug delivery system is intended primarily as a mechanical support for the matrix layer. In the simplest case, the matrix is exposed directly to the skin or membrane of the host, and the backing is a strip or patch capable of being secured to the skin, typically with the matrix acting as an adhesive. In such constructions, typically referred to as transdermal patches, the backing will usually be impermeable to the drug and the enhancer. Such impermeability inhibits the loss of the drug and enhancer and allows the user to rub the patch in order to promote release of the enhancer or drug from the polymeric particles, thus increasing the drug absorption rate. Suitable backing materials will generally be thin, flexible films or fabrics such as woven and non-woven fabrics and polymeric films, such as polyethylene, polypropylene, and silicone rubber; metal films and foils; and the like.

In a slightly more complex design, the matrix layer will be contained partly or wholly within an enclosure, where at least a portion of the enclosure is permeable to the drug and the enhancer. Typically, such enclosures will be formed from two or more different materials, where only the portion of the enclosure which interfaces with the skin or membrane of the host is formed from a permeable material. In that way, the remainder of the enclosure, which is impermeable to the drug and enhancer, inhibits loss of the drug and enhancer and allows the user to rub the transdermal device to increase the drug delivery rate. Suitable permeable membrane materials may be rate-limiting, that is they may limit the amount of drug which can cross the membrane and be transported across the patient's skin or membrane. More usually, however, the membrane will not be rate limiting, and the transdermal device will instead rely on the rate at which the enhancer and/or drug is released from the polymeric particles in order to determine the rate at which the drug is delivered to the patient.

Suitable permeable membrane materials may be selected based on the desired degree of permeability, the nature of the drug, the nature of the enhancer, and mechanical considerations related to constructing the device.

Exemplary permeable membrane materials include a wide variety of natural and synthetic polymers, such as polydimethylsiloxanes (silicone rubbers), ethylene-vinylacetate copolymer (EVA), polyurethanes, polyurethane-polyether copolymers, polyethylenes, polyamides, polyvinylchlorides (PVC), polypropylenes, polycarbonates, polytetrafluoro-ethylenes (PTFE), cellulosic materials, e.g., cellulose triacetate and cellulose nitrate/acetate, and hydrogels, e.g., 2-hydroxymethyl-methacrylate (HEMA).

The primary purpose of the matrix layer in the transdermal delivery systems of the present invention is to contain the polymeric particles which release the chemical penetration enhancer and/or drug into the matrix and to the skin or membrane of the host. Preferably, only the enhancer will be contained in the particles, while the drug is present directly in the matrix. The drug may be soluble, partially soluble, or insoluble in the matrix layer. Preferably, the drug is saturated, more preferably being supersaturated, in order to maximize the concentration and amount of drug provided in the delivery system. Usually, the drug will be much more soluble in the enhancer than in the matrix so that the matrix will not substantially inhibit diffusion of the drug therethrough. As the matrix will normally not control the drug delivery rate, the solubility of the drug within the matrix layer is not as critical a factor as in the design of many previous drug delivery systems. Similarly, the enhancer may be soluble, partially soluble, or insoluble in the matrix layer. Usually, the enhancer will be partially soluble or insoluble since this will minimize the amount of enhancer which is dissolved into the matrix prior to use. An enhancer which is insoluble in the matrix layer will promote retention of the enhancer within the polymeric particles, minimizing chemical interaction between the enhancer and the matrix material (as well as the drug). Moreover, release of the enhancer into the matrix layer will then be controlled by the kinetics of the polymeric particles. Once released into the matrix layer, the enhancer will dissolve the drug and diffuse to the matrix-skin interface where it will be able to increase transport of the drug (which is usually present in excess) across the skin or membrane barrier.

A wide variety of suitable materials for the matrix layer are available. Such materials should be biocompatible, capable of meeting purity standards required of medical devices, capable of being fabricated into a desired geometry, chemically stable (preferably being inert), and capable of being modified to provide for desired drug and enhancer transfer kinetics (typically by manipulating the degree of cross-linking, chemical structure, polymer blend, and plasticizer). Suitable materials include ethylene vinylacetate copolymers, cross-linked silicon rubbers, plasticized polyvinylchlorides, polyurethanes, microporous polypropylene, and the like.

The delivery system of the present invention is useful with practically all drugs which may be transdermally delivered to a host. In particular, the present invention will be useful with those drugs which require or are benefited by a chemical penetration enhancer in order to effect or increase transport of the drug across a skin or membrane barrier of a host.

Exemplary drugs which may be delivered by the system of the present invention include analgesics, anesthetics, anthelmintics, antidotes, antiemetics, antihistamines, antimalarials, antimicrobials, antipyretics, antiseptics, antituberculotics, antitussives, antivirals, cardioactive drugs, cathartics, chemotherapeutic agents, corticoids (steroids), depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasocontrictors, vasodilators, vitamins, xanthine derivatives, and the like.

Useful chemical permeability enhancers include lipophilic solvents, such as dimethylsulfoxide (DMSO), dimethyltoluamide, dimethylacetamide, dimethylformamide (DMF), and 2-pyrrolidone; two component systems, such as propylene glycol-oleic acid, and 1-4 butane diol-linoleic acid; cyclic alkyls, such as azacycloalkanes, e.g., 1-dodecylazacycloheptan-2-one (Azone®), alkyl morpholines, alkanoyl pyrrolidines, and cyclic ketones; esters, such as alkyl esters, prolylesters, and fatty acid esters, such as isopropylmyristate and diisopropyladipate; ionic and nonionic surfactants, such as acylated sarcosines, fatty acid monoalkylamides, and lauramide DEA; organic acids, such as citric acid and succinic acid; propylene glycol; propylenecarbonate; and urea.

It will be appreciated that the selection of drug, matrix layer material, and chemical penetration enhancer cannot be made independently. Rather, the nature of the drug and the enhancer are interdependent as the enhancer must be selected to provide for transport of that drug across the skin or membrane of the host. Additionally, the chemical and physical characteristics of the matrix material are also critical in a number of respects. Usually, the matrix layer material will be selected to be capable of acting as a reservoir for both the drug and the polymeric particles which contain the enhancer. In other cases, of course, it will be possible to contain the drug within particles to further promote compatibility with a wider range of matrix materials. Additionally, the solubility of the drug and/or enhancer in the matrix layer will determine both the amount of drug which can be contained therein as well as the transport characteristics of the enhancer from the polymeric particles to the device skin interface.

With these criteria in mind, the following list sets forth a number of compatible systems including the drug, matrix, and enhancer.

| Drug | Matrix | Enhancer |
| --- | --- | --- |
| Corticoid | Paraffinic | Propylene Glycol and/or Propylene Carbonate |
| Estradiol | Cross-linked Silicone rubber | Ethanol |
| Levonorgestrel | Ethylene Vinylacetate | Ethyl Acetate/ Ethanol |

Polymeric particles useful in the present invention each define a network of internal pores which contain the enhancer and/or drug. The nature of the particles is not critical, with rigid and elastic spherical and non-spherical, non-degradable and erodible, and open- and closed-pore particles all being suitable. In the exemplary embodiment, the polymeric particles are substantially non-collapsible beads having a cross-linking density of at least about 10%, more usually in the range from about 20% to 80%. The average bead diameter will range from about 5 $\mu$m to 100 $\mu$m, usually in the range from about 10 $\mu$m to 40 $\mu$m.

Conveniently, polymeric beads useful in the present invention may be formed by suspension polymerization of suitable monomers in an immiscible phase including a porogen. Generally, the monomers and the porogen are first mixed together, and the resulting mixture then suspended in the immiscible phase, usually an aqueous phase. The immiscible phase is then agitated to form droplets of the monomer mixture, and polymerization of the monomer mixture is initiated to form the desired beads. Once the beads are formed, the porogen may be extracted and the enhancer (and optionally drug) introduced by absorption. In some cases, however, it will be possible to utilize the enhancer as the porogen (or to combine the enhancer with a suitable porogen) so that the product of suspension polymerization may be used directly without extraction. The resulting beads are a dry powder which may be incorporated directly into the matrix layer, usually be conventional mixing techniques.

The polymeric particles may be rigid or elastic, spherical or non-spherical, non-degradable or erodible, and open-pore or closed-pore. The preparation of rigid beads is described in detail below, while the preparation of elastic particles (hydrogels) is described in numerous references, such as Kirk-Othmer, *Encyclopedia of Chemical Technology*, 3rd Ed., John Wiley & Sons, Vol. 15, pp. 656–675 (1981), and U.S. Pat. Nos. 4,058,491; 4,060,678; and 4,071,508. Most particle preparation processes will result in the formulation of spherical beads, but beads having non-spherical asymmetric, and/or irregular geometries will also find use so long as they meet the necessary physical parameters set forth below.

Suitable polymeric particles will not readily undergo unwanted reactions, will be stable over a wide pH range, and will resist moderate oxidation and reduction. The particles should be stable at higher temperatures and have a relatively long shelf life. Desirable physical parameters for the polymeric particles are as follows:

|  | Broad Range | Preferred Range |
| --- | --- | --- |
| Particle Size | 5–100 μm | 10–40 μm |
| Particle Density | 0.4–2.0 g/cc | 0.6–1.5 g/cc |
| Pore Volume | 0.1–2.0 cc/g | 0.3–1.0 cc/g |
| Pore Diameter | 0.001–3 μm | 0.003–1 μm |
| Surface Area | 1–500 m$^2$/g | 20–200 m$^2$/g |

The particles may be formed from a wide variety of polymers, including natural polymers such as carboxylmethylcellulose, cellulose acetate phthalate, ethylcellulose, methylcellulose, arabinogalactan, nitrocellulose, propylhydroxycellulose, and succinylated gelatin; and synthetic polymers such as polyvinyl alcohol, polyethylene, polypropylene, polystyrene, polyacrylamide, polyether, polyester, polyamide, polyurea, epoxy, ethylene vinyl acetate copolymer, polyvinylidene chloride, polyvinyl chloride, polyacrylate, polyacrylonitrile, chlorinated polyethylene, acetal copolymer, polyurethane, polyvinyl pyrrolidone, poly(p-xylene), polymethylmethacrylate, polyvinyl acetate, and polyhydroxyethyl methacrylate.

The preferred polymer particle matrix of the present invention comprises rigid polymeric beads having a substantially non-collapsible pore structure. That is, the beads will substantially retain their internal pore structure even after the porogen (used in formation of the bead as described hereinafter) has been extracted and the pores are empty. Such beads are mechanically stable compared with non-rigid materials, allowing manufacturing, processing, and handling of the beads under relatively rigorous conditions which might result in the rupture or damage of less stable materials. More importantly, the non-collapsible pores facilitate introduction of the chemical penetration enhancer and optionally drug precursor, as described in more detail hereinafter.

The rigid polymeric beads of the present invention are formed by polymerization and cross-linking of one or more preselected monomers to form a molecular structure having a substantially non-collapsible network of pores resulting from the presence of the porogen during polymerization. At least one monomer will be polyethylenically unsaturated, and usually the polymer will include a monoethylenically unsaturated co-monomer. The degree of cross-linking may then be controlled by adjusting the ratio of monoethylenically unsaturated monomer to polyethylenically unsaturated monomer, as discussed in more detail hereinbelow. The enhancer (and optionally drug) is entrapped within the network of pores, the resulting loaded particles act to release the enhance (and optionally drug) into the matrix layer at a preselected rate, depending on the physical characteristics of the particles as well as those of the enhancer and/or drug.

The rigid polymer beads of the present invention will have greater than 10% cross-linking, usually having in the range from about 20% to 80% cross-linking, more usually having in the range from about 25% to 60% cross-linking, and typically being in the range from about 45% to 55% cross-linking. The calculated or theoretical percentage of cross-linking is defined as the weight of polyethylenically unsaturated monomer (or monomers) divided by the total weight of monomer, including both polyethylenically unsaturated and monoethylenically unsaturated monomers.

The beads of the preferred polymer are conveniently formed by suspension polymerization in a liquid-liquid system. In general, a solution containing monomers, a polymerization catalyst (if used), and an inert but fully miscible liquid porogen is formed which is immiscible with water. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting rigid beads are recovered from the suspension. The beads at this point are solid porous structures, the polymer having formed around the inert, water-immiscible liquid, thereby forming the pore network. The liquid porogen has accordingly served as a "pore-forming agent" and occupies the pores of the formed beads.

Materials suitable as porogens will be liquid substances which meet the following criteria:

1. They are either fully miscible with the monomer mixture or capable of being made fully miscible by the addition of a minor amount of non-water-miscible solvent;
2. They are immiscible with water, or at most only slightly soluble;
3. They are inert with respect to the monomers, and stable when in contact with any polymerization catalyst used and when subjected to any conditions needed to induce polymerization (such as temperature and radiation); and
4. They are readily extracted from the pore network of the beads once polymerization is complete.

Suitable porogens include a wide range of substances, notably inert, non-polar organic solvents. Some of the most convenient examples are alkanes, cycloalkanes, and aromatics. Specific examples of such solvents are alkanes of from 5 to 12 carbon atoms, straight or branched chain cycloalkanes of from 5 to 8 carbon atoms, benzene, and alkyl-substituted benzenes, such as toluene and the xylenes. Extraction of the porogen may be effected by solvent extraction, evaporation, or similar conventional operations. The porogen extraction step accomplishes the removal of unwanted species from the polymerized structures prior to impregnation with the desired active substance. Such unwanted species include unreacted monomers, residual catalysts, and surface active agents and/or dispersants remaining on the bead surfaces.

Extraction of the porogen may be effected in a variety of ways, depending on the chemical nature of the porogen and its behavior in combination with that of the other species present. For example, the beads may be recovered from the suspension by filtration, preferably using vacuum apparatus (such as a Beuchner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used—i.e., where the porogen, unreacted monomer and water will form an azeotrope. In these cases, steam distillation is an effective way of extracting porogen from the beads. This again may be followed by drying under vacuum.

Once the beads are rendered dry and free of the porogen and any unwanted organic materials, melanin pigment is introduced to the internal pore networks of the individual beads by either an in situ oxidation procedure or by absorption of a melanin dispersion in a suitable solvent. These methods of introducing the melanin pigment will be described in more detail hereinbelow.

The polymerization process used in preparing the beads of the polymer delivery system can be modified to control both the porosity and the particle diameter of the beads. Particle diameter is controlled primarily by the degree of agitation, with more rigorous agitation causing smaller droplets and hence smaller polymerized beads. The pore diameter and pore volume, in contrast, are controlled primarily by the cross-linking density. Porosity is increased by increasing the amount of cross-linking monomer used, or by increasing the porogen concentration in the monomer mixture, or both. An increase in porosity increases the surface area of the bead and hence the weight percent of the melanin pigment which may be held within the bead. Bead diameter is also affected by the concentration of dispersing agent in the immiscible phase.

The bead diameter in the polymer delivery system should be in the range from about 5 to 100 microns. Beads having an average diameter in the range from about 5 microns to no more than about 70 microns are preferred, with a bead diameter in the range from about 10 microns to about 40 microns being particularly preferred.

The pore dimensions within the beads may vary widely, with optimum dimensions depending on the chemical characteristics of the polymers used as well as the diffusive characteristics of the active substance. Different systems will thus call for different optimum ranges of pore volume distribution to obtain the most desirable properties for the overall formulation. In general, however, best results are obtained with total pore volumes ranging from about 0.1 to about 2.0 cc/g, preferably from about 0.3 to about 1.0 cc/g; pore surface areas ranging from about 1 to about 500 $m^2/g$, preferably from about 20 to about 200 $m^2/g$; and average pore diameters ranging from about 0.001 to about 3.0 microns, preferably from about 0.003 to about 1.0 micron. Following conventional methods of measuring and expressing pore sizes, the pore diameters are measured by techniques such as nitrogen or mercury porosimetry and are based on the model of a pore of cylindrical shape.

In order to form the cross-linked polymer beads of the present invention, it is necessary to polymerize either polyethylenically unsaturated monomers, i.e., those having at least two sites of unsaturation, or to polymerize monoethylenically unsaturated monomers in the presence of one or more polyethylenically unsaturated monomers. In the latter case, the percentage of cross-linking may be controlled by balancing the relative amounts of monoethylenically unsaturated monomer and polyethylenically unsaturated monomer.

Monoethylenically unsaturated monomers suitable for preparing polymer beads for the polymer delivery system include ethylene, propylene, isobutylene, diisobutylene, styrene, ethylvinylbenzene, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isoprene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithioderivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl group of 1 to 2 carbon atoms substituted on the benzene nucleus; trivinylnaphthalenes, and polyvinylanthracenes.

The particularly preferred polymer delivery system of the present invention is formed by the copolymerization of methylmethacrylate and ethylene glycol dimethylmethacrylate. Usually, the methylmethacrylate will be present at from about 10 to 80 percent of the monomer mixture, more usually at about 20 to 60 percent of the monomer mixture, typically being in the range from about 45 to 55 percent of the monomer mixture, with the ethylene glycol dimethylmethacrylate forming the remainder of the mixture.

The chemical percutaneous enhancer (and optionally drug) is introduced to the polymeric particles either as the porogen (or as part of a porogen solution) in which case the enhancer-bearing particles are formed in a single step, or may be subsequently introduced by absorption into beads from which the porogen has been extracted. The preferred method of introduction will depend on the nature of the porogen, with one-step preparation techniques being suitable for enhancers which meet the requirements set forth above.

Most drugs, however, will be unsuitable for one-step preparation techniques and will thus be introduced to pre-formed particles by absorption of a suitable solution containing the drug. Once introduced to the particles, it may sometimes be desirable to evaporate the liquid carrier in order to leave the drug in solid form within the particles. Alternatively, the drug may be left in solution within the particles, particularly where the carrier is compatible with the material of the matrix layer.

The transdermal drug delivery systems of the present invention may utilize more than one type of particle in a single delivery device. For example, when both the enhancer and drug are incorporated in particles, it will frequently be desirable to employ different bead types to independently control the enhancer and drug release rates. Bead parameters such as diameter, pore size, pore volume, surface charge, composition, and the like, may be varied to achieve desired release rates for both the enhance and drug.

The bead characteristics may also be varied in order to achieve a prolonged period of release. For example a portion of the beads may be designed to release enhancer and/or drug over a first time period, e.g., 24 hours, while remaining portions can be designed to release over longer periods, e.g., 48 hours, 72 hours, etc. In this way, extended periods of release can be effected which would be impossible if only a single type of bead were employed.

The drug delivery system of the present invention may be utilized to treat virtually all types of vertebrate hosts in both veterinary and human therapeutic applications. Most often, transdermal delivery devices will be placed externally on the skin, either as part of an integral adhesive system or by separate taping or securing the device to the skin. In addition to such transdermal treatment systems, the drug delivery systems of the present invention may be used internally in the form of implants, oral lozenges, intrauterine devices, suppositories, ocular inserts, and the like. In the case of external applications, it will frequently be desirable for the host or medical practitioner to periodically rub the backing layer of the device in order to cause enhancer (and optionally drug) to be released from the polymeric particles into the matrix layer. From the matrix layer, the enhancer in the drugs will be readily available in order to effect transdermal transport of the drug to provide for systemic administration to the treated host.

Referring now to FIG. 1, a transdermal drug delivery system in the form of a transdermal patch includes a backing layer 12 and a matrix layer 14. The matrix layer 14 is formed from a suitable adhesive material, such as polyisobutylene or an acrylic, and includes a plurality of polymeric particles 16 dispersed throughout. The polymeric particles 16 will include at least the chemical penetration enhancer, while the drug to be administered may be present as a solid or liquid within either the matrix layer or within additional of the polymeric particles 16. The physical characteristics of the particle 16 may be identical or may vary, as described above. The transdermal patch 10 is applied by placing on a desired area of the host's skin so that adhesive matrix 14 is in close contact with the surface of the skin. If desired, the backing 12 may be rubbed in order to facilitate release of the enhancer and/or drug from the polymeric particles 16.

Referring now to FIG. 2, a monolithic transdermal delivery system 20 is illustrated. The monolithic system 20 is similar to the transdermal patch 10, except that a separate adhesive layer 22 is provided on the face of the matrix layer 24 and backing layer 26. Polymeric particles 28 are dispersed through the matrix layer 24 and optionally may be dispersed through the adhesive layer 22. As with the transdermal patch, the polymers will include at least the chemical penetration enhancer and may optionally contain the drug to be administered. The monolithic system 20 is applied by placing the adhesive layer 22 on the skin surface of the host. Both the drug and enhancer will be at least partially soluble in the adhesive layer to allow delivery from the matrix to the skin or membrane.

FIG. 3 illustrates a reservoir system 30 comprising an enclosure 32 and a matrix layer 34 within the enclosure. At least a portion of the enclosure 32 is formed from a material which is permeable to the drug and the enhancer. As before, polymeric particles 36 are dispersed throughout the matrix layer 34 and release enhancer (and optionally drug) into the matrix layer in a controlled manner. The drug may be present in the matrix layer or may be isolated within additional polymeric particles 36. The drug and enhancer eventually penetrate into their environment through the permeable portion of the enclosure 32. As illustrated in FIG. 3, the reservoir system 30 is suitable as an insert or lozenge to be utilized internally by the host.

The reservoir system 40 suitable for transdermal use is illustrated in FIG. 4. There, the enclosure comprises a backing layer 42 and a drug and enhancer permeable face layer 44. The backing layer 42 and face layer 44 are sealed about their edges and contain the matrix layer 46 therein. As with previous embodiments, the polymeric particles 48 are dispersed throughout the matrix layer and are capable of releasing enhancer and optionally, drug into the matrix layer. Adhesive material 50 is provided about the periphery of the face layer 44 in order to secure the system 40 to a host's skin. Optionally, the adhesive material could extend across the entire face layer 44 so long as it does not interfere with penetration of the drug through the host's skin.

Although the foregoing invention has been described in detail for purposes of clarity of understanding, it will be obvious that certain modifications may be practiced within the scope of the appended claims.

What is claimed is:

1. A device for the rate-controlled delivery of a drug, said device comprising:
    a matrix layer;
    means for mechanically supporting the matrix layer;
    a drug within the matrix layer; and
    a plurality of polymeric particles dispersed in the matrix layer, said particles each defining a network of internal pores which entrap and release a chemical penetration enhancer into the matrix layer at a release rate selected to control the rate at which the drug is systematically absorbed from the matrix by a host.

2. A device as in claim 1, further comprising means for removably securing the mechanical support means to a skin or membrane area of the host.

3. A device as in claim 2, wherein the means for securing comprises an adhesive surface.

4. A device as in claim 1, wherein the drug and the chemical penetration enhancer are both present within the polymeric particles.

5. A device as in claim 1, wherein the drug is contained in the polymeric particles while the enhancer is present directly in the matrix layer.

6. A device as in claim 1, wherein the polymeric particles comprise non-collapsible cross-linked beads prepared by suspension polymerization.

7. A device for the rate-controlled delivery of a drug, said device comprising:
- a matrix layer;
- means for mechanically supporting the matrix layer;
- a drug within the matrix layer;
- a chemical penetration enhancer within the matrix layer, wherein the chemical penetration enhancer has limited solubility within the matrix layer; and
- a plurality of polymeric particles dispersed in the matrix layer, said particles each defining a network of internal pores which entrap and release at least one of the chemical penetration enhancer and the drug into the matrix layer at release rates for said enhancer and/or said drug, whereby the rate of enhancer and/or drug release from the network of internal pores is selected to control the rate at which the drug is systematically absorbed by a host.

8. A device for the rate-controlled delivery of a drug, said device comprising:
- a matrix layer composed of a material selected from the group consisting of ethylene vinylacetate copolymers, cross-linked silicone rubbers, plasticized polyvinylchlorides and polyurethanes;
- means for mechanically supporting the matrix layer; and
- a plurality of polymeric particles dispersed in the matrix layer; said particles each defining a network of internal pores which entrap and release at least one of the chemical penetration enhancer and the drug into the matrix layer at release rates for said enhancer and/or said drug, whereby the rate of enhancer and/or drug release from the network of internal pores is selected to control the rate at which the drug is systematically absorbed by a host.

9. A device as in claim 1, wherein the drug is selected from the group consisting of analgesics, anesthetics, anthelmintics, antidotes, antiemetics, antihistamines, antimalarials, antimicrobials, antipyretics, antiseptics, antituberculotics, antitussives, antivirals, cardioactive drugs, cathartics, chemotherapeutic agents, corticoids (steroids), depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasocontrictors, vasodilators, vitamins, and xanthine derivatives.

10. A device as in claim 1, wherein the chemical penetration enhancer is selected from the group consisting of lipophilic solvents, two component systems, cyclic alkyls, azacycloalkanes, alkyl morpholines, alkanoyl pyrrolidines, cyclic ketones, fatty acid esters, ionic surfactants, non-ionic surfactants, organic acids, propylene glycol, propylenecarbonate, and urea.

11. A device as in claim 7, wherein the polymeric particles have a cross-linking density of at least about 10%.

12. A device as in claim 11, wherein the cross-linking density is in the range from about 20% to 80%.

13. A device for the rate-controlled delivery of a drug, said device comprising;
- a matrix layer;
- means for mechanically supporting the matrix layer;
- a drug within the matrix layer;
- a chemical penetration enhancer within the matrix layer; and
- a plurality of polymeric particles having an average diameter in the range from about 5 $\mu$m to 100 $\mu$m dispersed in the matrix layer, said particles each defining a network of internal pores which entrap and release at least one of the chemical penetration enhancer and the drug into the matrix layer at release rates for said enhancer and/or said drug, whereby the rate of enhancer and/or drug release from the network of internal pores is selected to control the rate at which the drug is systemically absorbed by a host.

14. A device as in claim 13, wherein the average diameter is in the range from about 10 $\mu$m to 40 $\mu$m.

15. A device as in claim 1, wherein the means for mechanically supporting the matrix layer comprises a backing.

16. A device as in claim 1, wherein the means for mechanically supporting the matrix comprises an enclosure, wherein at least a portion of the enclosure is permeable to the drug and the chemical penetration enhancer.

17. A device for the rate-controlled systemic delivery of a drug to a patient, said device comprising:
- a matrix layer;
- a plurality of polymeric particles dispersed in the matrix layer, said particles comprising non-collapsible, cross-linked structures defining a network of internal pores;
- a drug and a chemical penetration enhancer within the matrix layer, where at least one of the drug and enhancer is present within the pore networks of the polymeric particles, said drug and/or enhancer having a release rate from said pore networks selected to control the rate at which said drug is systemically delivered to the patient; and
- means for containing the matrix layer and exposing the matrix layer to a preselected skin or membrane area of the patient.

18. A device as in claim 17, wherein the means for containing and exposing is an enclosure having a permeable wall.

19. A device as in claim 18, wherein the permeable wall is a macroporous membrane which is not rate-limiting to the passage of the drug.

20. A device as in claim 17, wherein the percutaneous enhancer is present within the pore networks of the polymeric beads while the drug is not within the pore networks.

21. A device as in claim 17, wherein the percutaneous enhancer is present within the pore network of a first group of polymeric particles while the drug is present within the pore networks of a second group of polymeric particles.

22. A device as in claim 17, wherein the drug is present within the pore networks of the polymeric beads while the percutaneous enhancer is not within the pore networks.

23. The devices in claim 17, wherein the chemical penetration enhancer is selected from the group consisting of lipophilic solvents, two component systems, cyclic alkyls, azacycloalkanes, alkyl morpholines, alkanoyl pyrrolidines, cyclic ketones, fatty acid esters, ionic surfactants, non-ionic surfactants, organic acids, propylene glycol, propylenecarbonate, and urea.

24. A device as in claim 17, wherein the drug has limited solubility within the matrix.

25. A device as in claim 17, wherein the matrix layer is composed of a material selected from the group consisting of ethylene vinylacetate copolymers, cross-linked silicone rubbers, plasticized polyvinylchlorides and polyurethanes.

26. A device as in claim 18, wherein the drug is selected from the group consisting of analgesics, anesthetics, anthelmintics, antidotes, antiemetics, antihistamines, antimalarials, antimicrobials, antipyretics, antiseptics, antituberculotics, antitussives, antivirals, cardioactive drugs, cathartics, chemotherapeutic agents, corticoids, depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasocontrictors, vasodilators, vitamins, and xanthine derivatives.

27. A device as in claim 17, wherein the polymeric particles have a cross-linking density of at least about 10%.

28. A device as in claim 27, wherein the cross-linking density is in the range from about 20% to 80%.

29. A device as in claim 17, wherein the polymeric particles are beads having an average diameter in the range from about 5 $\mu m$ to 100 $\mu m$.

30. A device as in claim 29, wherein the average diameter is in the range from about 10 $\mu m$ to 40 $\mu m$.

31. A method for the systemic administration of a drug to a host, said method comprising:
 exposing a preselected skin or membrane area of the host to the drug, wherein the drug is present at a concentration which exceeds the absorptive capacity of the skin or membrane; and
 exposing the preselected skin or membrane area to a percutaneous enhancer capable of increasing the rate of absorption of the drug through the skin or membrane, wherein the rate of delivery of the enhancer to the skin or membrane is controlled in order to control the rate of systemic absorption of the drug.

32. A device as in claim 31, wherein the drug is selected from the group consisting of analgesics, anesthetics, anthelmintics, antidotes, antiemetics, antihistamines, antimalarials, antimicrobials, antipyretics, antiseptics, antituberculotics, antitussives, antivirals, cardioactive drugs, cathartics, chemotherapeutic agents, corticoids, depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasocontrictors, vasodilators, vitamins, and xanthine derivatives.

33. A method as in claim 31, wherein the chemical penetration enhancer is selected from the group consisting of lipophilic solvents, two component systems, cyclic alkyls, azacycloalkanes, alkyl morpholines, alkanoyl pyrrolidines, cyclic ketones, fatty acid esters, ionic surfactants, non-ionic surfactants, organic acids, propylene glycol, propylenecarbonate, and urea.

34. A method as in claim 31, wherein the rate of enhancer delivery is controlled by release from polymeric particles comprising non-collapsible cross-linked structures defining a network of internal pores which entrap and release the enhancer at a rate selected to effect a desired rate of systemic absorption.

35. A method as in claim 35, wherein the polymeric particles are present in a matrix layer which also contains the drug.

36. A method as in claim 35, wherein the drug is also contained within the polymeric particles within the matrix layer, said polymeric particles comprising non-collapsible cross-linked structures defining a network of internal pores which entrap and release the drug at a rate selected to effect a desired rate of systemic absorption.

* * * * *